United States Patent
Alekseev et al.

(10) Patent No.: US 10,054,613 B2
(45) Date of Patent: Aug. 21, 2018

(54) SCANNING PROBE MICROSCOPE COMBINED WITH A DEVICE FOR MODIFYING THE SURFACE OF AN OBJECT

(71) Applicant: PRIVATE INSTITUTION "NAZARBAYEV UNIVERSITY RESEARCH AND INNOVATION SYSTEM", Astana (KZ)

(72) Inventors: Alexander Alekseev, Astana (KZ); Aleksey Dmitriyevich Volkov, Astana (KZ); Dmitry Yuryevich Sokolov, Zelenograd Moscow (KZ); Anton Evgeniyevich Efimov, Moscow (RU)

(73) Assignee: PRIVATE INSTITUTION "NAZARBAYEV UNIVERSITY RESEARCH AND INNOVATION SYSTEM", Astana (KZ)

( * ) Notice: Subject to any disclaimer, the term of this patent is extended or adjusted under 35 U.S.C. 154(b) by 0 days.

(21) Appl. No.: 15/541,669

(22) PCT Filed: Jul. 10, 2015

(86) PCT No.: PCT/KZ2015/000010
§ 371 (c)(1),
(2) Date: Jul. 5, 2017

(87) PCT Pub. No.: WO2016/111608
PCT Pub. Date: Jul. 14, 2016

(65) Prior Publication Data
US 2017/0350921 A1    Dec. 7, 2017

(30) Foreign Application Priority Data

Jan. 5, 2015 (KZ) .................................. 2015/0001

(51) Int. Cl.
*G01Q 30/20* (2010.01)
*G01Q 10/00* (2010.01)

(52) U.S. Cl.
CPC ............. *G01Q 30/20* (2013.01); *G01Q 10/00* (2013.01)

(58) Field of Classification Search
CPC ........ B82Y 35/00; G01Q 10/00; G01Q 30/00; G01Q 30/02; G01N 1/06; G01N 1/28; G01N 1/42; B26D 5/00
See application file for complete search history.

(56) References Cited

U.S. PATENT DOCUMENTS 3,828,641 A * 8/1974 Sitte ......................... G01N 1/06
83/410
5,299,481 A * 4/1994 Lihl ......................... F25D 3/10
62/320
(Continued)

FOREIGN PATENT DOCUMENTS

EP      2 482 080 A1    8/2012
EP      2482080 A1  *   8/2012    ............. G01Q 30/20
(Continued)

OTHER PUBLICATIONS

International Search Report and Written Opinion dated Dec. 24, 2015 issued in corresponding application No. PCT/KZ2015/000010; w/ English partial translation and partial machine translation (13 pages).

*Primary Examiner* — David E Smith
(74) *Attorney, Agent, or Firm* — Westerman, Hattori, Daniels & Adrian, LLP

(57) ABSTRACT

The microscope for monitoring objects after nano-cutting and for investigating structures of macro- and micro-carriers under low temperature comprises a punch having a cutting edge, drives driving the punch along two axes, a platform rotatable in a plane, a piezo-scanner for recording a sample (Continued)

Figure 1:
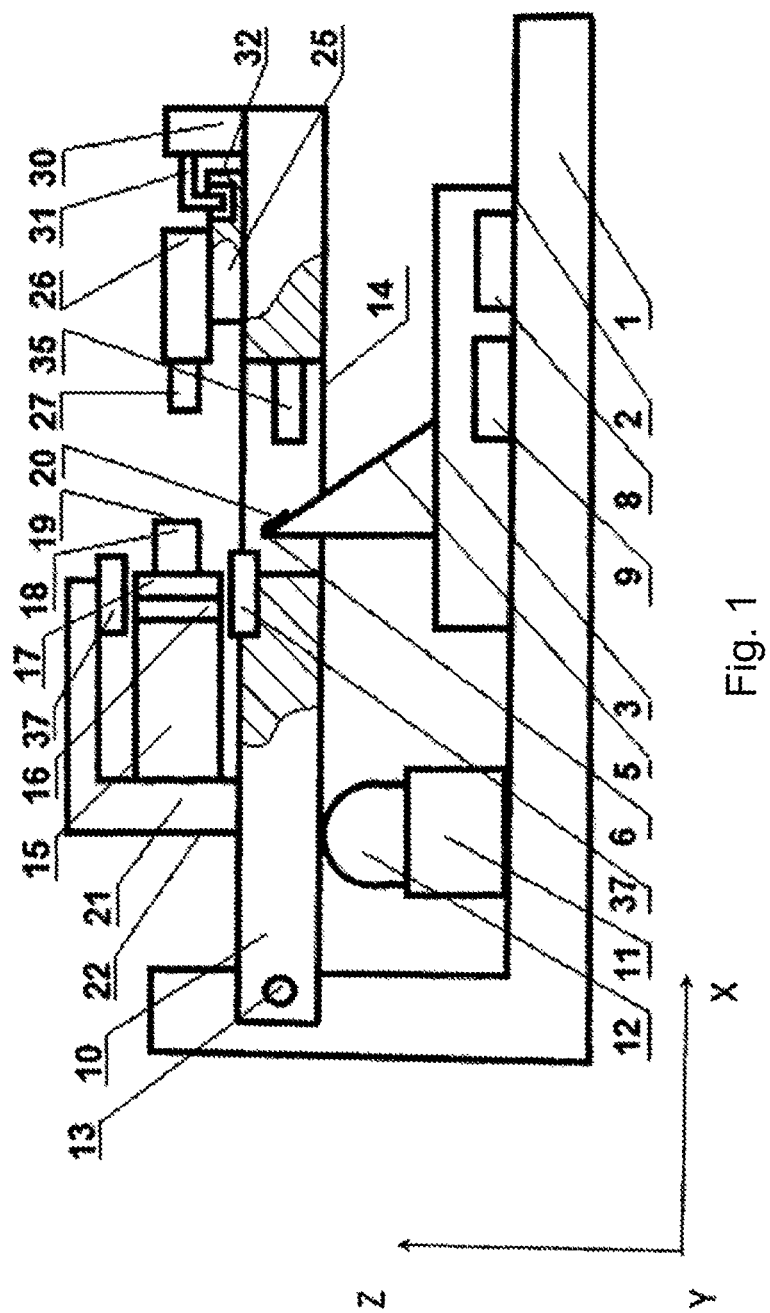

image along three axes, a holder with a carrier of the sample, and a probe unit to which a probe is fastened. The piezo-scanner is fastened to the platform, the punch is able to interact with the sample, and the probe unit is mounted on the platform so as to be movable along one of the axes. The assembly includes a module for mechanical action on the cutting edge of the punch to modify the cutting surface, which module is fastened to the same platform to which the piezo-scanner with the object carrier and the probe unit are fastened.

20 Claims, 4 Drawing Sheets

(56) References Cited

U.S. PATENT DOCUMENTS

| | | |
|---|---|---|
| 2009/0183613 A1 | 7/2009 | Lihl et al. |
| 2012/0223228 A1 | 9/2012 | Galloway |

FOREIGN PATENT DOCUMENTS

| | | | |
|---|---|---|---|
| KZ | 31337 B | 7/2016 | |
| RU | 2233490 C1 | 7/2004 | |
| RU | 2 248 628 C1 | 3/2005 | |
| RU | 2 282 257 C1 | 8/2006 | |
| RU | 2282257 C1 * | 8/2006 | ............. B82Y 35/00 |
| RU | 2287129 C2 | 11/2006 | |
| RU | 2 389 032 C2 | 5/2010 | |
| RU | 2427846 C1 | 8/2011 | |

* cited by examiner

SCANNING PROBE MICROSCOPE COMBINED WITH A DEVICE FOR MODIFYING THE SURFACE OF AN OBJECT

The scanning probe microscope combined with a device for modifying the surface of an object relates to measuring devices, particularly devices for monitoring objects using probes after nano-cutting and for investigating the structures of macro and micro-carriers under low temperature conditions.

A known example of prior art is a scanning probe microscope combined with a device for modifying the surface of an object comprising a foundation, onto which a punch module with a punch having a first cutting edge and an adjacent first surface, said punch module having a first drive for movement along a first X-axis and a second drive for movement along a second Y-axis, also comprising a platform installed on the foundation, movable along a third Z-axis and coupled with a third drive for movement along the third Z-axis, said Z-axis being orthogonal to the plane of XY axes, also comprising a piezo-scanner movable along the X, Y and Z axes with a holder with an object carrier containing the object, said piezo-scanner fastened to the platform, and the punch arranged so as to be able to interact with the object, also comprising a probe unit to which a probe is fastened, said probe unit fastened to the platform and movable along the first X-axis and coupled with the fourth drive for movement along the first X-axis, while the probe is able to interact with the object (Patent RU2389032. Scanning probe microscope combined with a device for modifying the surface of an object, May 10, 2010).

The drawback of the above device is that the piezo-scanner with the object is fastened to the platform which is flexibly installed on the foundation, while the probe unit with the probe is also installed on the foundation. Such arrangement creates a long mechanical "loop" between the object and the probe, comprising the piezo-scanner—the platform—the foundation—the probe unit. It increases mechanical noise level and lowers the accuracy of the probe measurement to impact the image quality.

Another example of prior art is a scanning probe microscope combined with a device for modifying the surface of an object, technical substance of said example being the nearest to the proposed technical solution, said microscope comprising a foundation, onto which a punch module with a punch having a first cutting edge and an adjacent first surface, said punch module having a first drive for movement along a first X-axis and a second drive for movement along a second Y-axis, also comprising a platform installed on the foundation, movable along a third Z-axis and coupled with a third drive for movement along the third Z-axis, said Z-axis being orthogonal to the plane of XY axes, also comprising a piezo-scanner movable along the X, Y and Z axes with a holder with an object carrier containing the object, said piezo-scanner fastened to the platform, and the punch arranged so as to be able to interact with the object, also comprising a probe unit with a probe holder to which a probe is fastened, said probe unit fastened to the platform and movable along the third X-axis and coupled with a fourth drive for movement along the first X-axis, while the probe is able to interact with the object (Application EP2482080. Scanning probe microscope combined with a device for modification of the object surface. Jan. 31, 2011).

The above device serves to solve the problem described and reduce the mechanical "loop". The above device is assumed herein as a prototype of the claimed solution. Its principal drawback is a lack of real-time means of control over the punch, the object and the piezo-scanner which reduces the image quality.

The object of the invention is to expand the functional capabilities of the scanning probe microscope combined with a device for modification of the object surface.

Technical result of the invention is increased image quality.

The stated technical result is achieved by introduction of a first module for mechanical action fastened to the same platform and able to interact with the punch to the scanning probe microscope combined with a device for modification of the object surface comprising a foundation, onto which a punch module with a punch having a first cutting edge and an adjacent first surface, said punch module having a first drive for movement along a first X-axis and a second drive for movement along a second Y-axis, also comprising a platform installed on the foundation, movable along a third Z-axis and coupled with a third drive for movement along the third Z-axis, said Z-axis being orthogonal to the plane of XY axes, also comprising a piezo-scanner movable along the X, Y and Z axes with a holder with an object carrier containing the object, said piezo-scanner fastened to the platform, and the punch arranged so as to be able to interact with the object, also comprising a probe unit with a probe holder to which a probe is fastened, said probe unit fastened to the platform and movable along the first X-axis and coupled with a fourth drive for movement along the first X-axis, while the probe is able to interact with the object, with the following options of arrangement of the module components:

- option 1—the first module for mechanical action is installed so as to be able to interact with the first cutting edge of the punch;
- option 2—the first module for mechanical action is installed so as to be able to interact with the first surface of the punch;
- option 3—the first module for mechanical action is installed so as to be able to interact with the first cutting edge and the first surface of the punch;
- option 4—at least one second module for mechanical action is introduced, said module installed on the platform so as to be able to interact with an object module;
- option 5—the second module for mechanical action is installed so as to be able to interact with the object;
- option 6—the second module for mechanical action is installed so as to be able to interact with the object holder;
- option 7—the second module for mechanical action is made of flexible material and installed so as to be able to interact with the piezo-scanner;
- option 8—the first module for mechanical action includes a first heating unit;
- option 9—the first module for mechanical action includes a first piezo-module;
- option 10—the first module for mechanical action includes a second cutting edge;
- option 11—the first module for mechanical action includes a sharpened point;
- option 12—the first module for mechanical action includes an area having a rough surface;
- option 13—the second module for mechanical action includes a second heating unit.
- option 14—the second module for mechanical action includes a second piezo-module.

option 15—it is introduced a piezo unit fastened to the probe unit, onto which a probe holder is installed.

option 16—the piezo-unit is arranged so as to be able to move along the first X-axis and the third Z-axis.

option 17—the piezo-unit is arranged so as to be able to move along the first X-axis and the second Y-axis.

option 18—the piezo-unit is arranged so as to be able to move along the first X-axis, the second Y-axis and the third Z-axis.

option 19—the foundation with all components is placed in a cryo chamber.

Figure 6:
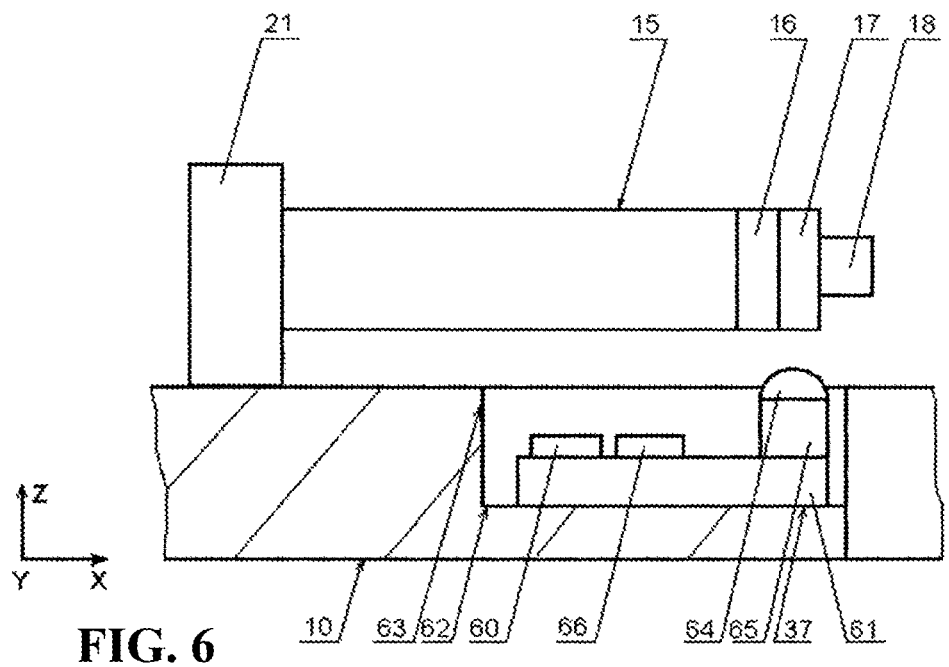
Figure 7:
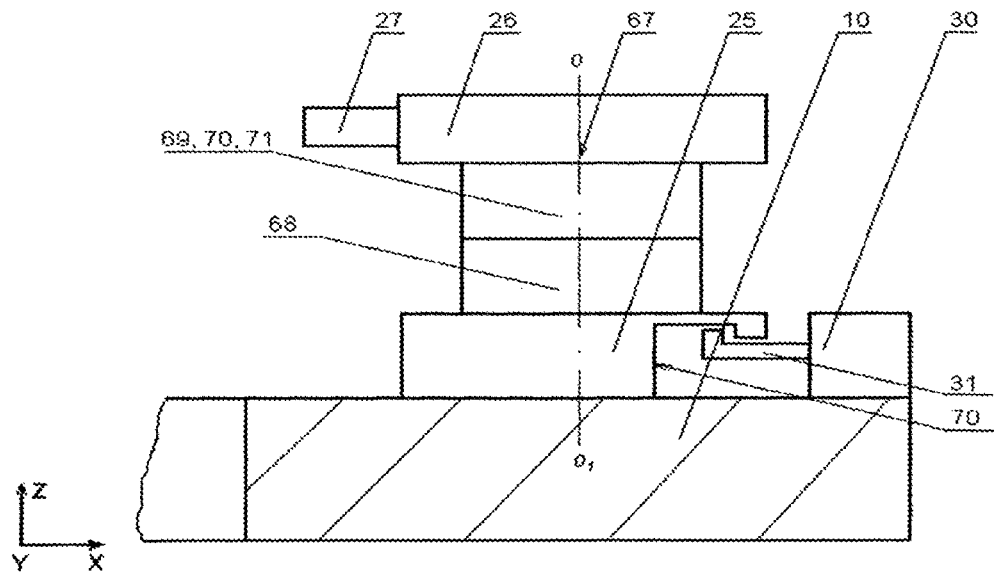
Figure 8:
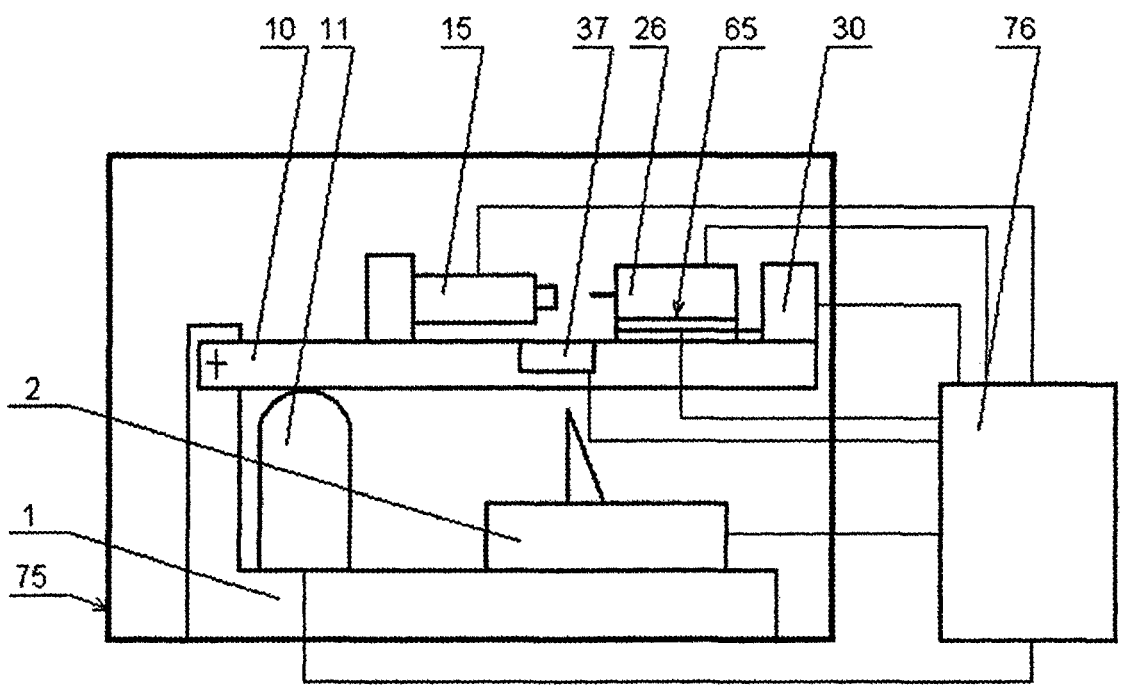

The essence of the invention is further illustrated by the following drawings:

FIG. 1—a general view of the scanning probe microscope combined with a device for modification of the object surface;

FIGS. 1-5—options of a first module for mechanical action;

FIG. 6—option of a second module for mechanical action;

FIG. 7—option of piezo unit operation;

FIG. 8—diagram showing the use of the scanning probe microscope combine with a device for modification of the object surface as part of a cryo microtome.

A scanning probe microscope combined with a device for modification of the object surface comprises a foundation 1, see FIG. 1, onto which a punch module 2 with a punch 3 is fastened. The punch 3 comprises a first cutting edge 4 and an adjacent first surface 5 and a second surface 6. The punch module 2 comprises a first drive 8 for movement along a first X-axis and a second drive 9 for movement along a second Y-axis. The scanning probe microscope combined with the device for modification of the object surface also comprises a platform 10 installed on the foundation 1, movable along a third Z-axis and coupled with a third drive 11, said third drive comprising a first push rod 12, for movement along the third Z-axis orthogonal to the plane of the XY axes. The platform 10 is fastened to the foundation 1 by a hinge 13 and has a sampling unit 14. The scanning probe microscope combined with a device for modification of the object surface also comprises a piezo scanner 15, movable along the X, Y and Z axes and having a holder 16 with an object carrier 17 containing an object 18 comprising a surface 19. Said piezo scanner is fastened to the platform 10 using an adapter 21, while the punch 3 is installed so as to be able to interact with the object 18. Components 15, 16, 17, 18, 21 are the module of the object 22. The object 18 can be fastened to the object carrier 17 using glue, for example, epoxy resin. The object carrier 17 can be fastened to the object holder 16 using a magnet. For this purpose, the holder 16 can be manufactured, for instance, from the samarium-cobalt alloy. An alternative is to include an insert made of the above alloy (not shown). The object carrier 17 can be made from nickel. The scanning probe microscope combined with the device for modification of the object surface also comprises a probe unit 25 with a probe holder 26 inside which a probe 27 is mounted, said probe unit 25 is installed on the platform 10, movable along the first X axis and coupled with a fourth drive 30 for movement along the first X-axis via the second push rod 31, while the probe 27 is able to interact with the object 18. A quartz crystal resonator is generally used as the probe 27. The fourth drive 30 can be installed on the platform 10 and must ensure that the probe unit 25 is movable in two opposite directions along the X axis thanks to the second push rod 31 being located in a first groove 32. An option of the invention involves the fourth drive 30 fastened to the foundation 1 and operationally coupled with the probe unit 25. This can be done by moving the platform along the Z axis and inserting and removing the second push rod 31 from the first groove (not shown). A first module for mechanical action 35 is introduced to the scanning probe microscope combined with the device for modification of the object surface as an independent feature, said module fastened to the platform 10 and able to interact with the punch 3.

Components 1, 2, 3, 10, 11, 12, 13 are standard components a micro cryotome described in /1, 2, 3, 4/. Components 15, 16, 17, 18, 21, 22, 25, 26, 27, 30, 31, 32 are standard components of any scanning probe microscope and are described in /1, 2/. The scanning probe microscope combined with a device for modification of the object surface operates as follows. The object carrier 17 containing the object 18 is fastened to the holder 16. The probe holder 26 containing the probe 27 is fastened to the probe unit 25. The platform 10 is lowered to the punch 3 using the third drive 11, and the object 18 is cut to form the surface 19 and the fragmented object 20. Following that, the platform 10 is raised to the topmost position using the drive 11. The probe 27 approaches the surface 19 of the object 18 using the fourth drive 30. Then the surface 19 is scanned relative to the probe 27 and the topography of the surface 19 is measured using a piezo-scanner 15. The components can be arranged as follows.

Option 1—the module for mechanical action 35 is installed so as to be able to interact with the first cutting edge 4 of the punch 3. This option is executable where the first cutting edge 4 and the first module for mechanical action 35 are positioned in the same plane by moving the platform 10 along the Z axis using the third drive 11. Then the first cutting edge 4 and the first module for mechanical action 35 are brought together using the first drive 8. When they interact, the cutting edge 4 can be modified to improve its quality and, consequently, to improve the quality of the section and the resulting image.

Option 2—the module for mechanical action 35 is installed so as to be able to interact with the first surface 5 of the punch 3. This option is executable where the first cutting edge 4 and the first module for mechanical action 35 are positioned in the different planes by moving the platform 10 along the Z axis using the third drive 11. Then the first surface 5 and the first module for mechanical action 35 are brought together using the first drive 8. When they interact, the first surface 5 can be modified to improve its quality and, consequently, to improve the quality of the section and the resulting image.

Option 3—the module for mechanical action 35 is installed so as to be able to interact with the first cutting edge 4 and the first surface 5 of the punch 3. This option is executable where, for example, after the first surface 5 and the first module for mechanical action 35 are brought together, the platform 10 is moved along the Z axis together with the punch 3 along the X axis to carry out operational interaction of the first module for mechanical action 35 and the first cutting edge 4. This makes it easier to modify the cutting edge 4 and the first surface 5 of the punch at the same time.

Option 4—at least one second module for mechanical action 37 is introduced and installed on the platform 10 so as to be able to interact with the object module 22. The first option involves fastening of the second module for mechanical action 37 between the piezo-scanner 15 and the punch 3 (bottom position). The second option involves fastening of the second module for mechanical action 37 at the opposite side of the piezo-scanner 15 relative to the punch 3 using an adapter (topmost position). Both the first and the second positional options can be utilized at the same time.

Option 5—the second module for mechanical action 37 is installed so as to be able to interact with the object 18 by moving the same along the Z axis and the X axis. A possibility of interaction of the second module for mechanical action 37 with the object 18 in the second positional option allows to support the object 18 during cutting to improve the quality of the cut and the result image quality.

Option 6—the second module for mechanical action 37 is installed so as to be able to interact with the object carrier 17 by moving the same along the Z axis and the X axis. The fact that the module for mechanical action 37 is installed so as to be able to interact with the object carrier 17 allows moving the same along the surface of the holder 16 to make it easier to find a required area on the surface 19 of the object 18. This solution also serves to make the device more reliable for the purpose of the second positional option of the second module for mechanical action 37 by ensuring that the piezo-scanner 15 remains intact during cutting of the object 18.

Option 7—the second module for mechanical action 37 is made of elastic material and installed so as to be able to interact with the piezo-scanner 15 by moving the same along the Z axis and the X axis. Viton can be utilized as such elastic material. This solution makes it possible to adjust the quality factor of the piezo scanner 15 during scanning to improve the image quality.

Figure 2:
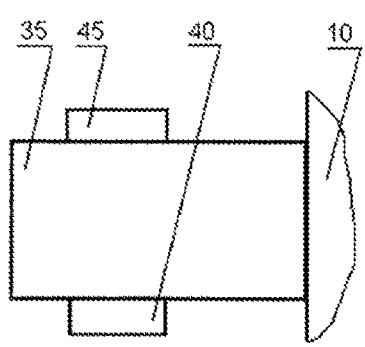

Option 8—the first module for mechanical action 35 includes a first heating unit 40, see FIG. 2. An Atos microheater [5] or a Peltier element [6] can be used as such heater. This solution makes it possible to remove frost and moisture from the punch in the event of contact between the first module for mechanical action 35 and the punch 3 to improve the quality of the cut and the resulting image quality.

Option 9—the first module for mechanical action 35 includes a first piezomodule 45. A piezoelectric plate connected to the alternating voltage supply can be used as such piezomodule. This solution makes it possible to remove eventual contaminations from the punch 3 in the event of contact between the first module for mechanical action 35 and the punch 3 to improve the quality of the cut and the resulting image quality.

Figure 3:
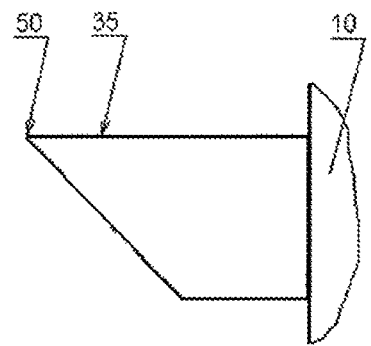

Option 10—the first module for mechanical action 35 includes a second cutting edge 50, see FIG. 3. This solution makes it possible to separate the fragments of the sample 20 that may have stuck to the first surface 5 using the second cutting edge 50, and to facilitate removal of the same from the surface 5 to improve the quality of the cut and the resulting image quality.

Figure 4:
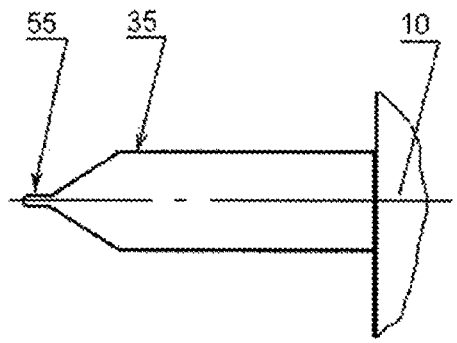

Option 11—the first module for mechanical action 35 includes a sharpened point 55, see FIG. 4. This solution makes it possible to catch the fragments 20 that may have stuck to the first surface 5 and remove them to improve the quality of the cut and the resulting image quality. If the sharpened point 55 is made of a springy organic material, for example, polystyrene, and has a diameter of 0.1-0.3 mm, contaminations can be removed directly from the first cutting edge 4 with no risk of damaging it.

Figure 5:
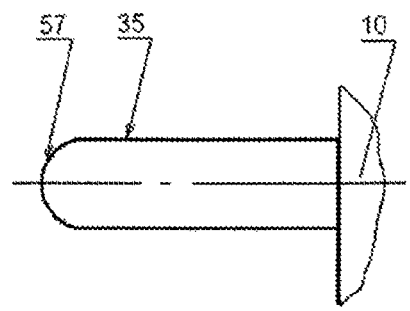

Option 12—the first module for mechanical action 35 includes the area 57, see FIG. 5, having a rough surface. This solution makes it possible to catch the fragments 20 that may have stuck to the first surface 5 and remove them (move them away) to improve the quality of the cut and the resulting image quality. If such area 57 is made of Viton, contaminations can be removed directly from the first cutting edge 4 with no risk of damaging it.

Option 13—the second module for mechanical action 37 includes a second heating unit 60, see FIG. 6. This solution makes it possible to remove frost and moisture from the object in the event of contact between the second module for mechanical action 37 and the object 18 to improve the quality of the cut and the resulting image quality. For this purpose, the base plate 61 is moved along the X axis along the surface 62 of the sampler 63. This can be performed manually in the locking screw grooves (not shown). Following that, the piezo-scanner touches the contact element 64 of the second module for mechanical action 37 and the object 18 by inclining it along the Z axis. Another option involves contact between the contact element 64 of the second module for mechanical action 37 and the object 18 using a moving device 65 which can either be a pneumatic drive or a piezo drive. The second positional option shown in the FIG. 1 (topmost position) of the second module for mechanical action 37 is not shown in the FIG. 6. This option functions in the similar way.

Option 14—the second module for mechanical action 37 includes a second piezomodule 66 which can take the form of a piezoelectric plate connected to an alternating voltage supply. This solution makes it possible to remove eventual contaminations from the object in the event of contact between the second module for mechanical action 37 and the object 18 to improve the quality of the cut and the resulting image quality.

Option 15—wherein the device comprises a piezo unit 67, see FIG. 7, fastened to the probe unit 25, onto which the probe holder 26 is installed. The piezo unit 67 can be made of a piezo tube and installed on the probe unit 25, with the symmetry axis O-O1 located along the Z axis. The FIG. 7 shows an alternative view of the push rod 31 and a second groove 70 as compared to the FIG. 1. The option shown in the FIG. 7 have a slight advantage over the option shown in the FIG. 1 due to the fact that the second groove 70 will attract less (than the first groove 32) contaminations from the above to make the contacts between the probe and the sample 18 more accurate.

Option 16 (option one)—wherein the piezo unit 67 is arranged so as to be able to move along the first X-axis and the third Z-axis (option one). This solution makes it possible to dedicate a motion area 68 along the Z axis on the probe unit 25, while the probe holder 26 will be installed in the motion area 69 along the X axis.

Option 17 (option two)—wherein the piezo-unit 67 is arranged so as to be able to move along the second Y-axis and the third Z-axis (option two). This solution makes it possible to dedicate a motion area 68 along the Z axis on the probe unit 25, while the probe holder 26 will be installed in the motion area 70 along the Y axis.

Option 18 (option three)—wherein the piezo-unit 67 is arranged so as to be able to move along the first X-axis, the second Y-axis and the third Z-axis (option three). This solution makes it possible to dedicate a motion area 68 along the Z axis on the probe unit 25, while the probe holder 26 will be installed in the motion area 71 along the X, Y axes. This solution of the piezo unit 67 is structurally similar to the piezo-scanner 45. Multiple options of piezo unit 67 are described in detail in /7/. Such arrangements make it possible to scan both the first surface 5 with fragments 20 and the surface 19 to expand the functionality of the invention. Option one may be supplemented with moving the punch along the Y axis using the second drive 9 to examine the first cutting edge 4 and the first surface 5 more carefully, remove contaminations in due time and improve image quality. The option two allows to examine fragments 20 in more detail, for example, thickness, which is an important parameter for setting the cut thickness. The option three combines both previous options. It should be noted that if the piezo unit 67 takes the form of a piezo tube with its longitudinal axis O-O1 located along the Z axis, it facilitates examination of the first surface 5 inclined against the Z axis. This effect is attributable to the fact that piezo tubes generally have a much lower range of axial movement (Z) as compared to the orthogonal plane movements (X, Y).

Some of the options involve placing the scanning probe microscope combined with the device for modification of the object surface inside a cryo chamber 75, see FIG. 8. Components 2, 11, 15, 26, 37, 65 are connected to the control unit 76. This makes it possible to cut "soft" objects.

REFERENCES

1. Patent RU2389032. Scanning probe microscope combined with a device for modification of the object surface, May 10, 2010.
2. Application EP2482080. Scanning probe microscope combined with a device for modification of the object surface. Jan. 31, 2011.
3. U.S. Pat. No. 5,299,481. Carrier arm seal for a microtome of ultramicrotome. Apr. 5, 1994.
4. Patent US2009183613. Micromanipulator for a cryomicrotome. July 23, 23.
5. http://atos.ru.
6. http://russian.alibaba.com
7. Patent RU2248628. Multifunctional piezo-scanner and method of scanning in probe microscopy, Mar. 20, 2005.

The invention claimed is:

1. Scanning probe microscope combined with a device for modification of the object surface, comprising:
   a foundation, onto which a punch module with a punch having a first cutting edge and an adjacent first surface is arranged, the punch module having a first drive for movement along a first X-axis and a second drive for movement along a second Y-axis,
   a platform installed on the foundation, movable along a third Z-axis and coupled with a third drive for movement along the third Z-axis, said Z-axis being orthogonal to the plane of XY axes,
   a piezo-scanner movable along the X, Y and Z axes with a holder with an object carrier containing an object, the piezo-scanner being fastened to the platform, and the punch being arranged so as to be able to interact with the object, and
   a probe unit with a probe holder to which a probe is fastened, the probe unit being fastened to the platform and movable along the first X-axis and coupled with a fourth drive for movement along the first X-axis, while the probe is able to interact with the object, and
   a first module for mechanical action, the first module being fastened to the platform so as to be able to interact with the punch.

2. The scanning probe microscope according to claim 1, wherein the first module for mechanical action is installed so as to be able to interact with the first cutting edge of the punch.

3. The scanning probe microscope according to claim 1, wherein the first module for mechanical action is installed so as to be able to interact with the first surface of the punch.

4. The scanning probe microscope according to claim 1, wherein the first module for mechanical action is installed so as to be able to interact with the first cutting edge and the first surface of the punch.

5. The scanning probe microscope according to claim 1, which includes at least one second module for mechanical action, fastened to the platform so as to be able to interact with an object module.

6. The scanning probe microscope according to claim 5, wherein the second module for mechanical action is installed so as to be able to interact with the object.

7. The scanning probe microscope according to claim 5, wherein the second module for mechanical action is installed so as to be able to interact with the object carrier.

8. The scanning probe microscope according to claim 5, wherein the second module for mechanical action is made of elastic material and installed so as to be able to interact with the piezo-scanner.

9. The scanning probe microscope according to claim 1, wherein the first module for mechanical action includes a first heating unit.

10. The scanning probe microscope according to claim 1, wherein the first module for mechanical action includes a first piezo unit.

11. The scanning probe microscope according to claim 1, wherein the first module for mechanical action includes a second cutting edge.

12. The scanning probe microscope according to claim 1, wherein the first module for mechanical action includes a sharpened point.

13. The scanning probe microscope according to claim 1, wherein the first module for mechanical action includes an area having a rough surface.

14. The scanning probe microscope according to claim 5, wherein the second module for mechanical action includes a second heating unit.

15. The scanning probe microscope according to claim 5, wherein the second module for mechanical action includes a second piezo unit.

16. The scanning probe microscope according to claim 1, which includes a piezo unit, fastened to the probe unit onto which the probe holder is installed.

17. The scanning probe microscope according to claim 16, wherein the piezo unit is arranged so as to be able to move along the first X-axis and the third Z-axis.

18. The scanning probe microscope according to claim 16, wherein the piezo unit is arranged so as to be able to move along the first X-axis and the second Y-axis.

19. The scanning probe microscope according to claim 16, wherein the piezo unit is arranged so as to be able to move along the first X-axis, the second Y-axis and the third Z-axis.

20. The scanning probe microscope according to claim 1, wherein the foundation with all components is placed inside a cryo chamber.

* * * * *